(12) United States Patent
Embry

(10) Patent No.: US 8,663,225 B2
(45) Date of Patent: Mar. 4, 2014

(54) HYDROGEL BONE VOID FILLER

(75) Inventor: Jill M. Embry, Somerville, TN (US)

(73) Assignee: Medtronic, Inc., Minneapolis, MN (US)

( * ) Notice: Subject to any disclaimer, the term of this patent is extended or adjusted under 35 U.S.C. 154(b) by 1902 days.

(21) Appl. No.: 10/987,817

(22) Filed: Nov. 12, 2004

(65) Prior Publication Data

US 2006/0106392 A1    May 18, 2006

(51) Int. Cl.
*A61F 2/28* (2006.01)

(52) U.S. Cl.
USPC ............................................. 606/76

(58) Field of Classification Search
USPC ............................ 606/76, 910; 424/422, 423; 623/23.61–23.62
See application file for complete search history.

(56) References Cited

U.S. PATENT DOCUMENTS

| | | | |
|---|---|---|---|
| 4,186,448 A | 2/1980 | Brekke | |
| 4,357,384 A * | 11/1982 | Jasperson | 428/215 |
| 4,547,327 A | 10/1985 | Bruins et al. | |
| 4,803,075 A * | 2/1989 | Wallace et al. | 424/423 |
| 4,904,257 A * | 2/1990 | Mori et al. | 106/161.1 |
| 4,968,542 A | 11/1990 | Gasper et al. | |
| 5,007,940 A * | 4/1991 | Berg | 424/423 |
| 5,116,387 A * | 5/1992 | Berg | 523/113 |
| 5,158,573 A * | 10/1992 | Berg | 523/113 |
| 5,266,326 A | 11/1993 | Barry et al. | |
| 5,274,074 A | 12/1993 | Tang et al. | |
| 5,294,446 A | 3/1994 | Schlameus et al. | |
| 5,318,554 A | 6/1994 | Young et al. | |
| 5,356,629 A * | 10/1994 | Sander et al. | 424/422 |
| 5,451,406 A * | 9/1995 | Lawin et al. | 424/423 |
| 5,468,787 A | 11/1995 | Braden et al. | |
| 5,472,775 A | 12/1995 | Obijeski et al. | |
| 5,486,593 A | 1/1996 | Tang et al. | |
| 5,505,952 A | 4/1996 | Jiang et al. | |
| 5,508,036 A | 4/1996 | Bakker et al. | |
| 5,549,679 A | 8/1996 | Kuslich | |
| 5,571,189 A | 11/1996 | Kuslich | |
| 5,624,727 A | 4/1997 | Stoy | |
| 5,626,861 A * | 5/1997 | Laurencin et al. | 424/426 |
| 5,645,592 A | 7/1997 | Nicolais et al. | |
| 5,658,592 A | 8/1997 | Tanihara et al. | |
| 5,736,160 A | 4/1998 | Ringeisen et al. | |
| 5,770,229 A | 6/1998 | Tanihara et al. | |
| 5,795,922 A | 8/1998 | Demian et al. | |

(Continued)

FOREIGN PATENT DOCUMENTS

| | | |
|---|---|---|
| EP | 1418188 | 5/2004 |
| EP | 1642602 | 4/2006 |

(Continued)

OTHER PUBLICATIONS

Dalton et al. "Manufacture of poly(2-hydroxyethyl methacrylate-co-methyl methacrylate) hydrogel tubes for use as nerve guidance channels" Sep. 2002, Biomaterials, 23(18): 3843-51.*

(Continued)

*Primary Examiner* — Christian Sevilla
(74) *Attorney, Agent, or Firm* — Sorell Lenna & Schmidt LLP

(57) ABSTRACT

A bone void filler material, including a hydrogel component provided by microparticulates of pre-set hydrogel material dispersed within a carrier component to maintain the microparticulates substantially proximate to one another so that the resulting fill material is rendered as a substantially flowable mass.

19 Claims, 1 Drawing Sheet

(56) References Cited

U.S. PATENT DOCUMENTS

Figure 1:
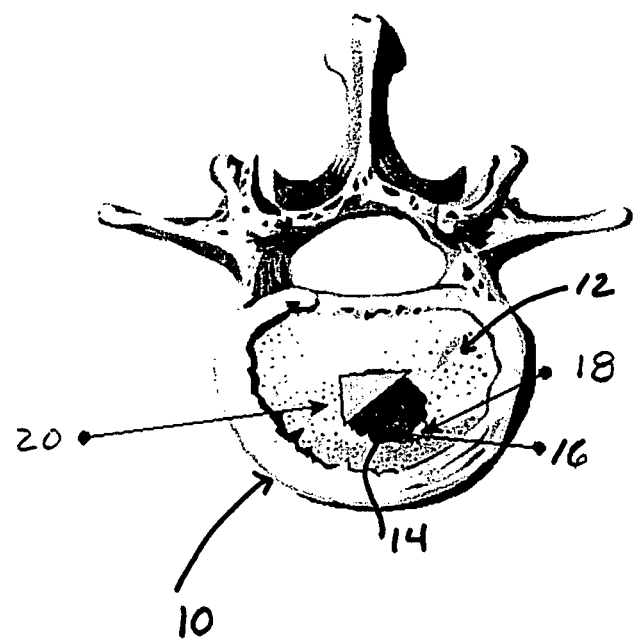

| | | | |
|---|---|---|---|
| 5,820,918 A | 10/1998 | Ronan et al. | |
| 5,840,290 A * | 11/1998 | Hench et al. | 424/423 |
| 5,856,367 A | 1/1999 | Barrows et al. | |
| 5,876,743 A | 3/1999 | Ibsen et al. | |
| 5,900,245 A | 5/1999 | Sawhney et al. | |
| 5,935,594 A | 8/1999 | Ringeisen et al. | |
| 5,980,883 A | 11/1999 | Tanihara et al. | |
| 6,027,744 A | 2/2000 | Vacanti et al. | |
| 6,063,061 A | 5/2000 | Wallace et al. | |
| 6,086,863 A | 7/2000 | Ritter et al. | |
| 6,171,610 B1 | 1/2001 | Vacanti et al. | |
| 6,174,683 B1 * | 1/2001 | Hahn et al. | 435/6.12 |
| 6,231,615 B1 * | 5/2001 | Preissman | 623/23.73 |
| 6,262,034 B1 | 7/2001 | Mathiowitz et al. | |
| 6,268,405 B1 | 7/2001 | Yao et al. | |
| 6,340,477 B1 | 1/2002 | Anderson | |
| 6,352,710 B2 | 3/2002 | Sawhney et al. | |
| 6,376,573 B1 | 4/2002 | White et al. | |
| 6,387,391 B1 | 5/2002 | Shikinami et al. | |
| 6,425,923 B1 | 7/2002 | Stalcup et al. | |
| D464,135 S | 10/2002 | Hawkins | |
| 6,458,147 B1 | 10/2002 | Cruise et al. | |
| 6,458,375 B1 * | 10/2002 | Gertzman et al. | 424/423 |
| 6,458,889 B1 | 10/2002 | Trollsas et al. | |
| 6,531,147 B2 | 3/2003 | Sawhney et al. | |
| 6,565,960 B2 * | 5/2003 | Koob et al. | 428/304.4 |
| 6,579,533 B1 | 6/2003 | Törmälä et al. | |
| 6,613,018 B2 | 9/2003 | Bagga et al. | |
| 6,613,798 B1 | 9/2003 | Porter et al. | |
| 6,629,947 B1 * | 10/2003 | Sahatjian et al. | 604/13 |
| 6,630,351 B1 | 10/2003 | Monahan et al. | |
| 6,638,621 B2 | 10/2003 | Anderson | |
| 6,679,886 B2 | 1/2004 | Weikel et al. | |
| 6,680,046 B1 * | 1/2004 | Boschetti | 424/9.1 |
| 6,703,047 B2 | 3/2004 | Sawhney et al. | |
| 7,419,482 B2 * | 9/2008 | Nash et al. | 604/507 |
| 2001/0049413 A1 * | 12/2001 | Haraguchi | 524/446 |
| 2002/0032447 A1 | 3/2002 | Weikel et al. | |
| 2002/0035401 A1 | 3/2002 | Boyce et al. | |
| 2002/0123750 A1 | 9/2002 | Eisermann et al. | |
| 2004/0024460 A1 | 2/2004 | Ferree | |
| 2004/0044410 A1 | 3/2004 | Ferree et al. | |
| 2004/0087956 A1 | 5/2004 | Weikel et al. | |
| 2004/0097980 A1 | 5/2004 | Ferree | |
| 2004/0133208 A1 | 7/2004 | Weikel et al. | |
| 2004/0133275 A1 | 7/2004 | Mansmann | |
| 2004/0158227 A1 * | 8/2004 | Nash et al. | 604/500 |
| 2004/0158311 A1 * | 8/2004 | Berhow et al. | 623/1.15 |

FOREIGN PATENT DOCUMENTS

| | | |
|---|---|---|
| WO | WO 96/01598 | 1/1996 |
| WO | WO 01/17574 A1 | 3/2001 |
| WO | WO 2004043438 | 5/2004 |
| WO | WO 2004098756 | 11/2004 |
| WO | WO 2005115488 | 12/2005 |

OTHER PUBLICATIONS

Otani et al. "Hemostatic capability of rapidly curable glues from gelatin, poly(L-glutamic acid), and carbodiimide" Nov. 1998, Biomaterials, 19(22): 2091-8.*

Gorman, Beyond Jell-O: New ideas gel in the lab; Science News Online, vol. 161, No. 21, p. 323, May 25, 2002.

Rosiak et al., Radiation Formation of Hydrogels for Biomedical Application; IAEA REport, Oct. 18, 2004.

* cited by examiner

HYDROGEL BONE VOID FILLER

FIELD OF THE INVENTION

This invention relates generally to bone treatment agents. More particularly, this invention relates to bone treatment agents for introduction into bone voids and particularly compressed vertebral bodies for maintaining the height of compressed vertebral bodies and inhibiting further collapse.

BACKGROUND AND SUMMARY OF THE INVENTION

Vertebroplasty and kyphoplasty are examples of surgical procedures for treating fractured and diseased bones. In these procedures a bone void fill material or filler, such as a bone cement, is introduced, as by injection, into the fractured bone, e.g., the vertebral body. Improvement is desired in the composition of bone void fillers.

In this regard, the invention relates to a bone void filler material that incorporates a hydrogel component provided by microparticulates made of a pre-set, e.g., fully polymerized, hydrogel, dispersed within a carrier component, preferably provided by an adhesive, to maintain the hydrogel particulates proximate to one another so that the fill material is a substantially cohesive and flowable mass. The bone void fill material may be introduced, such as via a needle, into a void of a bone, such as a cavity within a vertebral body during a vertebroplasty procedure.

The microparticulates of the hydrogel component are substantially a solid, but swell upon exposure to body fluids to substantially fill the vertebral body. The carrier component helps to maintain the microparticulates proximate to one another and yield a flowable, injectable mass that remains cohesive within the bone void.

In another aspect, the invention relates to a method of filling a bone void. The method includes the steps of providing microparticulates of a pre-set hydrogel material; providing a flowable carrier; dispersing the microparticles within the carrier component to render a substantially flowable mass; and flowably introducing the mass of microparticles dispersed within the carrier component into a bone void.

DETAILED DESCRIPTION

The invention relates to bone treatment agent, preferably a bone void filler, that is suitable for use in filling voids in bony structures and for treatment of fractured bone. In particular, the treatment agent is configured for use in surgical procedures wherein the agent is introduced into compressed vertebral bodies for treatment of the compressed vertebral bodies to fill void areas and aid in at least partially restoring the height of the patient and for inhibiting further collapse of the vertebral body. In particular, the treatment agents of the invention are preferably utilized in conjunction with vertebral lift devices such as described in U.S. application Ser. No. 10/987,180, entitled IMPLANTABLE VERTEBRAL BODY LIFT and filed concurrently herewith.

In a preferred embodiment, the invention provides a biocompatible bone void fill material that includes a pre-set or pre-solidified hydrogel component and an carrier component. In this regard, it will be understood that the hydrogel component is provided by microparticulates of pre-set or polymerized hydrogel material and the carrier component, preferably an adhesive, maintains the microparticulates substantially proximate so that the resulting fill material is rendered as a substantially flowable mass.

The bone void fill material may be flowably introduced, such as via a needle, into a void of a bone, such as a cavity within a vertebral body during a vertebroplasty procedure. The hydrogel microparticulates swell upon exposure to body fluids to substantially fill the vertebral body. The carrier component helps to maintain the hydrogel components proximate to one another to yield a flowable composition and to provide a substantially cohesive fill material.

In this regard, and with reference to FIG. 1, there is shown a vertebral body, such as a vertebra lumbalis 10, having a void 12. A quantity of fill material 14 is shown within the void 12. The fill material 14 includes a hydrogel component provided by microparticulates 16 made of pre-set hydrogel material and a carrier component 18. An enclosure of mesh 20 is preferably also provided within the void 12 for receiving the fill material 14.

Hydrogels are networks of polymer chains that are set or solidified so as to form a three-dimensional structure that is substantially insoluble in water and which is highly hydrophillic so that when exposed to water it absorbs water and swells. The polymers may be natural or synthetic polymers and setting or solidification of the polymeric chains may be accomplished by various well-known mechanisms, such as by crosslinking and by coagulation. Thus, it will be understood that the hydrogel components utilized in the bone void fill material of the invention are pre-set or pre-solidified or polymerized prior to their introduction into the body.

The hydrogel component is preferably made of non-biodegradable polymers, examples of which include polyacrylic acid polymers, polyethylene glycol polymers such as polyethylene glycol co polyethylene oxide, hydrophillic segmented urethanes, polyvinylpyrrolididone, polyvinylacrylate, polymethacrylic acid and polymethacrylates, and PLA-PEG copolymers. The hydrogel component may also preferably be made of biodegradable polymers, examples of which inlude poly($\alpha$-hydroxyesters), poly(L-lactic acid), poly(DL-lactic acid), and poly(dl-lactic-co-glycolic acid).

The pre-set hydrogel components for use in the present invention are preferably provided as microparticles, such as microspheres, preferably ranging in size from about 50 to about 500 microns.

Preparation of hydrogel microparticles such as microspheres and the like may be accomplished by well known techniques such as solvent emulsion or solvent evaporation, microdispersion, interfacial polymerization, coacervation, cryogenic grinding, and suspension. For example, in solvent emulsion or evaporation, the polymer is dissolved in an organic solvent and suspended in an aqueous phase that contains a surface active agent. The resulting emulsion is stirred as the organic solvent evaporates, leaving solid microspheres.

The carrier component is preferably provided by an adhesive material, most preferably cellulose and/or bioadhesive polymers such as cyanoacrylate and flowable gelatin hydrogels including gelatin-gluteraldehyde, gelatin-poly (L-glutamic acid) (PLGA), and gelatin-alginate-carbodiimide. In the case of the use of gelatin hydrogels as carrier agents, these materials may be polymerized or subsequently polymerized after introduction into the body. The carrier component is formulated as a suspension into which the pre-set hydrogel component may be dispersed.

In a preferred embodiment, the bone void fill material preferably contains the pre-set hydrogel component and the carrier component in amounts such that the percentage (by weight) of the carrier component to the hydrogel component ranges from about 5 to about 15 percent. The resulting bone void fill material preferably has an elastic modulus of from about 15 to about 25 Gpa and a compressive strength of from about 5 to about 20 Mpa.

The pre-set hydrogel component and the carrier component may be combined as by pre-mixing in a syringe or via a dual-barrel syringe that mixes the streams at the syringe/needle interface. In the event unpolymerized gelatin hydrogel is selected as the carrier material, the gelatin hydrogel material may be suspended in an alginate solution and combined with a sodium chloride solution introduced into the syringe to initiate a crosslinking reaction to polymerize the carrier component in situ.

The bone void fill material may also preferably include additives such as biocompatible fibrous materials, such as carbon fibers, to provide mechanical reinforcement to the bone void filler material. Other preferred fibrous materials for use as additives include nitinol fibers and coils, polyurethane fibers and coils, stainless steel fibers and nylon. Preferred fibers have a length of from about 200 microns to about 1 mm, and a width of from about 25 microns to about 50 microns. The fibers are preferably incorporated when combining the hydrogel and adhesive components.

In addition, if it is desired to render the filler material radiopaque, a radiopacifier material may be included. Examples of radiopacifier materials include gold, tantalum, and barium compositions such as barium sulfate. The radiopacifier materials are generally available in a powder form and may be encapsulated into the pre-set hydrogel microparticles or mixed in with the adhesive suspension.

Other preferred additives include pharmacological agents such as growth factors, proteins, amino acids, polysaccharides, and antibiotics and other pharmaceutics. Preferred growth factors include fibroblast growth factors (FGF), bone morphogenetic growth factors (BMP), and platelet-derived growth factors (PDGF). Preferred proteins include collagen and herapin. Preferred polysaccharides include glycosaminoglycon (GAG). Preferred pharmaceutics include biophosphates such as pamidronate. These additives may be encapsulated or crosslinked to side chains of the pre-set hydrogel microparticles.

Accordingly, the foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A bone void filler material, consisting essentially of:
a hydrogel component provided by microparticles of pre-set hydrogel material dispersed within a flowable gelatin hydrogel carrier component of an adhesive suspension and biocompatible fibrous materials in a mesh enclosure to maintain the microparticles proximate to one another so that the resulting fill material is rendered as a substantially flowable mass to fill and remain a cohesive mass within a void in a bony structure; wherein the carrier component comprises gelatin-gluteraldehyde.

2. The filler material of claim 1, wherein the microparticles range in size from about 50 to about 500 microns.

3. The filler material of claim 1, wherein the microparticles are non-biodegradable polymers.

4. The filler material of claim 1, wherein the microparticles are non-biodegradable polymers selected from the group consisting of polyacrylic acid polymers, polyethylene glycol polymers, hydrophillic segmented urethanes, polyvinylpyrolididone, polyvinylacrylate, polymethacrylic acid and polymethacrylates, and PLA-PEG copolymers.

5. The filler material of claim 1, wherein the microparticles are biodegradable polymers.

6. The filler material of claim 1, wherein the microparticles are biodegradable polymers selected from the group consisting of poly($\alpha$-hydroxyesters), poly(L-lactic acid), poly(DL-lactic acid), and poly(dl-lactic-co-glycolic acid).

7. The filler material of claim 1, wherein the percentage (by weight) of the carrier component to the hydrogel component is from about 5 to about 15 percent.

8. A method of filling a bone void, the method comprising the step of providing the bone filler material of claim 1.

9. A vertebroplasty bone void filler material, consisting essentially of:
a hydrogel component provided by microparticles of pre-set hydrogel material dispersed within a flowable gelatin hydrogel carrier of an adhesive suspension and biocompatible fibrous materials in a mesh enclosure to maintain the microparticles proximate to one another to fill and remain a cohesive mass within a void in a bony structure with a vertebral body;
wherein the carrier component comprises gelatin-gluteraldehyde.

10. The filler material of claim 9, wherein the microparticles range in size from about 50 to about 500 microns.

11. The filler material of claim 9, wherein the microparticles are non-biodegradable polymers.

12. The filler material of claim 9, wherein the microparticles are non-biodegradable polymers selected from the group consisting of polyacrylic acid polymers, polyethylene glycol polymers, hydrophillic segmented urethanes, polyvinylpyrrolididone, polyvinylacrylate, polymethacrylic acid and polymethacrylates, and PLA-PEG copolymers.

13. The filler material of claim 9, wherein the microparticles are biodegradable polymers.

14. The filler material of claim 9, wherein the microparticles are biodegradable polymers selected from the group consisting of poly($\alpha$-hydroxyesters), poly(L-lactic acid), poly(DL-lactic acid), and poly(dl-lactic-co-glycolic acid).

15. The filler material of claim 9, wherein the filler material further comprises one or more additives selected from the group consisting of radiopacifier materials, and pharmacological agents.

16. The filler material of claim 1, wherein the carrier component is configured to polymerize after introduction into the void in the bony structure.

17. The filler material of claim 1, wherein the biocompatible fibrous materials comprise at least one of carbon fibers, nitinol fibers and coils, stainless steel fibers and nylon.

18. The filler material of claim 17, wherein the biocompatible fibrous materials have a length of from about 200 microns to about 1 mm and a width of from about 25 microns to about 50 microns.

19. The filler material of claim 1, further comprising growth factors.

* * * * *